US012699088B2

(12) United States Patent
Alsheimer

(10) Patent No.: US 12,699,088 B2
(45) Date of Patent: Aug. 4, 2026

(54) CONNECTOR, MARKER AND METHOD FOR ANALYSING BIOLOGICAL SAMPLES

(71) Applicant: LEICA MICROSYSTEMS CMS GMBH, Wetzlar (DE)

(72) Inventor: Soeren Alsheimer, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 726 days.

(21) Appl. No.: 18/158,497

(22) Filed: Jan. 24, 2023

(65) Prior Publication Data

US 2023/0258628 A1    Aug. 17, 2023

(30) Foreign Application Priority Data

Jan. 25, 2022    (EP) ..................................... 22153210
Feb. 1, 2022     (EP) ..................................... 22154515

(51) Int. Cl.
G01N 33/543    (2006.01)
G01N 33/58     (2006.01)
(52) U.S. Cl.
CPC ..... G01N 33/54306 (2013.01); G01N 33/582 (2013.01); G01N 2458/10 (2013.01)
(58) Field of Classification Search
CPC ......... G01N 33/54306; G01N 2458/10; G01N 33/582
See application file for complete search history.

(56) References Cited

U.S. PATENT DOCUMENTS

2013/0316376 A1    11/2013    Hedhammar et al.
2020/0040382 A1     2/2020    Beechem et al.

FOREIGN PATENT DOCUMENTS

WO    WO 2015/017586 A1    2/2015
WO    WO 2018/094385 A1    5/2018
WO    PCT/EP2021/06        6/2021
            6645
WO    WO-2021141924 A1 *   7/2021    ....... G01N 33/54353
WO    WO 2022/242887 A1    11/2022

OTHER PUBLICATIONS

Chiu et al. (Antibody Structure and Function: The Basis for Engineering Therapeutics, Antibodies, 2019) (Year: 2019).*
Steffen Frey, Dirk Görlich, "A new set of highly efficient, tag-cleaving proteases for purifying recombinant proteins," Journal of Chromatography A, vol. 1337, Feb. 19, 2014, pp. 95-105, Elsevier, Netherlands.

* cited by examiner

*Primary Examiner* — Heather Calamita
*Assistant Examiner* — Elizabeth Rose Lafave
(74) *Attorney, Agent, or Firm* — LEYDIG, VOIT & MAYER, LTD.

(57) ABSTRACT

A connector is provided for analysing biological samples including at least one first affinity reagent configured to bind directly or indirectly to a target molecule, and a backbone connected to the first affinity reagent and having at least one first affinity interactor, wherein the first affinity interactor is configured to specifically bind to a second affinity interactor having a label in order to bind the label to the backbone, and wherein the backbone has a cleavage site for irreversibly separating the first affinity reagent and the first affinity interactor. In a further aspect, a marker and a method for analysing biological samples are provided.

15 Claims, 7 Drawing Sheets

716

714

700

712

706

718

714

702

712

708

720

714

704

712

710

CONNECTOR, MARKER AND METHOD FOR ANALYSING BIOLOGICAL SAMPLES

CROSS-REFERENCE TO PRIOR APPLICATION

This application claims benefit to European Patent Application Nos. 22154515.5, filed on Feb. 1, 2022, and 22153210.4, filed on Jan. 25, 2022, the entire disclosures of both of which are hereby incorporated by reference herein.

TECHNICAL FIELD

The invention relates to a connector, a marker, and a method for analysing biological sample, in particular for imaging analysis of the biological sample.

BACKGROUND

In order to address key problems in the field of life sciences it is vital to precisely identify and to locate certain structures or target molecules within biological samples, e.g. tissue samples or cell cultures. This can be done by introducing markers into the sample that only bind to specific structures, e.g. specific biomolecules. These markers typically comprise an affinity reagent that only attaches to the structure in question and one or more fluorescent dyes or labels that are either directly conjugated to the affinity reagent or attached to the affinity reagent by other means, for example a secondary affinity reagent.

Fluorescence microscopy for example allows for imaging the sample with high spatial resolution but generally involves only a low number of different fluorescent dyes, typically between 1 and 5. The available dyes have to be distributed to all markers that are used to identify cell types, functional markers like protein-of-interest and general morphological markers in the same experiment. This means that only a limited number of structures can be marker by unique fluorescent dyes and thus identified at the same time. This further means that different cell types can only be poorly identified in most imaging experiments. While modern approaches that allow for a much more reliable and robust identification of cell types, e.g. based on the analysis of genetic regulatory networks (GRNs), exist, they require a much higher number of different markers to be read-out from the sample. While documents PCT/EP2021/066645 and PCT/EP2021/073819 disclose methods for analysing biological samples with a large number of fluorescent molecules at the same time, generating a diverse set of markers with different affinities and labels with varying fluorescent properties remains time consuming and expensive.

SUMMARY

In an embodiment, the present invention provides a connector for analysing biological samples including: at least one first affinity reagent configured to bind directly or indirectly to a target molecule, and a backbone connected to the first affinity reagent and comprising at least one first affinity interactor. The first affinity interactor is configured to specifically bind to a second affinity interactor comprising a label in order to bind the label to the backbone, and the backbone comprises a cleavage site for irreversibly separating the first affinity reagent and the first affinity interactor.

BRIEF DESCRIPTION OF THE DRAWINGS

Hereinafter, embodiments are described referring to the drawings, wherein.

DETAILED DESCRIPTION

Figure 1:
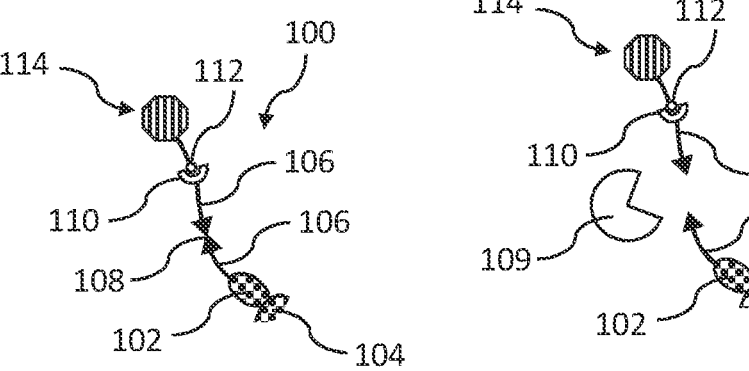
FIG. 1 shows a schematic view of a connector for analysing biological samples.

Provided herein are a connector, a marker and a method for analysing biological samples that allow for generating markers and analysing the samples at a low cost and time expenditure.

In an embodiment, a connector is provided for analysing biological samples comprising at least one first affinity reagent configured to bind directly or indirectly to a target molecule; a backbone connected to the first affinity reagent and comprising at least one first affinity interactor; wherein the first affinity interactor is configured to specifically bind to a second affinity interactor comprising a label in order to bind the label to the backbone; wherein the backbone comprises a cleavage site for irreversibly separating the first affinity reagent and the first affinity interactor with the label. The label may, in particular, be optically detectable. The target molecule is a particular structure of the biological sample, for example, a protein of the biological sample, a small molecule (e.g. lactic acid), or a mRNA molecule of the biological sample. Further examples are peptides, small molecules, metabolites, hormones, neurotransmitters, metal ions. The biological sample may be, for example, tissue, bodily fluids, a solid biopsy, a liquid biopsy, embryos (e.g. zebrafish, *Drosophila*), model organisms (e.g. zebrafish larvae, *Drosophila* embryos, *C. elegans*), cells (e.g. prokaryotes, eukaryotes, archaea), multicellular organisms (e.g. Volvox), suspension cell cultures, monolayer cell cultures, 3D cell cultures (e.g. spheroids, tumoroids, organoids derived from various organs such as intestine, brain, heart, liver), a lysate of any of the aforementioned, or a virus.

Thus, in certain embodiments, the connector comprises in order: the first affinity reagent, the backbone with the cleavage site, and the first affinity interactor.

The binding between the first affinity reagent and the target molecule may be specific, in particular. That means, that the first affinity reagent only binds to the target molecule. However, when the binding is indirect, the first affinity reagent may only bind to a further entity, which in turn binds only to the target molecule. Thus, in this case, the first affinity reagent binds indirectly only to the target molecule.

In certain embodiments, the first affinity interactor may only bind to the second affinity interactor. This binding may be irreversible at physiological conditions.

In particular, this may further overcome disadvantages with current solutions, for example: In particular, the present invention enables generating connectors using monovalent (first) affinity reagents such as for example a nanobody, a single-chain antibody, an aptamer, an oligonucleotide, or a small molecule compound, which is combined with a backbone that comprises a cleavage site for dye inactivation and an affinity interactor, which is used to mediate the high affinity interaction or coupling of the connector to the label. This design has many advantages, for example it is possible to construct fully peptide-based or fully-nucleotide based connectors, which allows their synthesis in one go or their expression from a single expression cassette. This makes manufacturing particularly easy, cost-efficient and reproducible. Owing to this design scheme, only the label needs to be coupled to the second affinity interactor using standard coupling chemistries. This can, however, be done by a manufacturer in larger scale. For the (end-)user, the design has a key advantage in multiplexing applications, in which users commonly need to perform coupling of labels to the primary antibodies that they intend to use in a study, which can easily be >100 antibodies. Performing >100 coupling reactions is a tedious, manual process connected to significant batch-to-batch variability. Using connectors described herein, users may simply pre-incubate a suitable connector with a second affinity reagent (e.g. the primary antibody) to connect the second affinity reagent to the connector. This can be performed by simply mixing connectors and antibodies in a multi-well plate, which is easily automated using standard laboratory automation and liquid handling equipment such as pipetting robots or dispensers.

Preferably, the first affinity reagent is a nanobody, a single domain antibody, an aptamer, a small-molecule, or an oligonucleotide. This enables particularly easy assembly of the connector and binding to the target molecule with high affinity and specificity.

More preferably, when the first affinity reagent is configured to bind indirectly to the target molecule, the connector comprises a second affinity reagent bound to the first affinity reagent, and the second affinity reagent is configured to (directly) bind to the target molecule. This enables particularly flexible assembly and use of the connector, for example, in combination with several antibodies of the same isotype.

Preferably, the second affinity reagent is an antibody and the first affinity reagent is configured to bind to a fragment crystallisable region (Fc region) of the antibody. This enables binding to the target molecule with particularly high affinity and specificity. In particular, the first affinity reagent may be a nanobody.

It is preferred, that the backbone comprises an oligonucleotide or a peptide. For example, the backbone may be DNA-origami-based or a nanoruler. This enables easy assembly and efficient production of the backbone.

Preferably, the cleavage site is a photocleavable cleavage site. This enables easy cleaving of the cleavage site.

In a preferred embodiment the backbone is cleavable specifically at the cleavage site by a site specific enzyme, for example TEV protease, caspase, Factor Xa or a restriction enzyme, cleavage light, for example UV light, or by a temperature change. Specifically, this causes cleaving of covalent bonds of the backbone with restriction enzyme or proteolytic enzyme, UV light; or melting/denaturing of hybridised oligonucleotide backbone. This enables efficient cleaving of the cleavage site.

Preferably, the first affinity interactor and the second affinity interactor are configured to form a bioconjugate. This means that the first and second affinity interactor may covalently bind to each other. Examples of pairs of interactors that form bioconjugates are spytag/spycatcher, snooptag/snoopcatcher and dogtag/dogcatcher. This enables robust and specific binding of the first and second affinity interactor to each other.

Preferably, the first affinity interactor is one of biotin or streptavidin and the second affinity interactor is the other one of biotin or streptavidin. This enables robust and specific binding of the first and second affinity interactor to each other.

More preferably, the connector comprises a plurality of first affinity interactors for binding one second affinity interactor each.

Preferably, the label comprises at least a first fluorophore. This enables detection of the label by an optical read-out device such as a microscope.

In another embodiment a marker is provided for analysing biological samples comprising the connector according to one of the preceding claims and further comprising a second affinity interactor with a label. The second affinity interactor with the label is bound to first affinity interactor to connect the label to the connector. The label may in particular comprise at least one fluorophore. The fluorophore may, for example, be a fluorescent protein, a fluorescent molecule, or a fluorescent quantum dot.

In a further embodiment a method is provided for analysing a biological sample comprising the following steps: providing, in particular, generating, at least a first set of markers, wherein the first set of markers comprises at least a first plurality of connectors configured to bind directly or indirectly to a first target molecule, and each first connector comprising a first label; introducing at least the first set of markers into the sample in order for the markers to bind to their respective target molecule in the sample; directing excitation light onto the biological sample, the excitation light being configured to visualise or excite at least the first label; and generating at least one optical readout from light emitted by at least the first label. The marker may comprise only the first affinity reagent or additionally the second affinity reagent, thus the first target molecule may be bound directly by the first affinity reagent or indirectly by the second affinity reagent. The label may be bound to the connector by the first and second affinity interactors.

In order to introduce the marker into the sample, the sample may be permeabilised. Further, the marker may be introduced into the sample as individual parts or as with the parts bound together prior. Preferably, when the marker comprises the connector with the first affinity reagent and the label, the individual parts may be introduced individually into the sample. However, when the marker comprises the connector with the first and the second affinity reagent and the label, the individual parts may be assembled or bound together prior to introduction into the sample.

The optical readout may be generated by means of a read-out device capable of fluorescence multicolour reading or imaging. A readout device typically includes at least one excitation light source, a detection system including at least one detection channel and may contain filters and/or dispersive optical elements to route excitation light to the sample and/or to route emission light from the sample onto a detector. In particular, the read-out device may be a fluorescent microscope.

Further, optional washing steps may be included, for example, after introduction of the marker into the sample, in order to remove unbound markers.

Preferably, the first set of markers further comprises at least a second plurality of connectors configured to bind directly or indirectly to a second target molecule, and each second connector comprising a second label. The second target molecule is bound by the first affinity reagent of the second connector. This enables analysing a larger number of target molecules.

It is preferred, that the first label and the second label have different fluorescent properties. In particular, the label is a fluorophore. The fluorescent properties may include an excitation wavelength/spectrum, an emission wavelength/spectrum and an emission duration or fluorescence lifetime. This enables distinguishing between the first and the second label.

Preferably, in a step e) the cleavage site of the connectors of at least the first set of markers is cleaved. For example, cleaving may be achieved by addition of an enzyme, or by illuminating the markers with UV light. The cleaving results in separating the label from the marker. This enables blanking of the markers, meaning the fluorescent signal is removed from the markers.

Preferably, in a step f) the cleaved off second affinity interactor is removed with the label from the biological sample. This may be achieved by washing the sample with buffer, for example. This enables removing background fluorescence of the cleaved labels.

Preferably, the steps a) to d) are repeated with a second set of markers, wherein the second set of markers comprises at least a third plurality of connectors configured to bind directly or indirectly to a third target molecule, and each connector comprising a third label.

The method and the marker may have the same advantages as the connector described herein. In particular, the method and the marker may be supplemented using the features of the connector described herein.

Further features and advantages of the invention result from description of preferred embodiments herein, which are described at least in part with reference to the accompanying drawings.

FIG. 1 shows a schematic view of a connector 100 for analysing biological samples. The connector 100 comprises a first affinity reagent 102, which is configured to specifically and directly bind to a target molecule 104. The first affinity reagent 102 is a nanobody, for example.

In addition, the connector 100 comprises a backbone 106 connected to the first affinity reagent 102. The backbone 106 comprises a cleavage site 108 for irreversibly separating the backbone 106 into two parts 106', 106", for example, by an enzyme 109.

Moreover, the backbone comprises at least one first affinity interactor 110. The first affinity interactor 110 is configured to specifically bind to a second affinity interactor 112 comprising a label 114, in order to enable the binding of the label 114 to the backbone 106 of the connector 100. The first affinity interactor 110 and the second affinity interactor 112 can thus bind to each other specifically. Upon binding, the second affinity interactor 112 with the label 114 is connected to the connector 100. The binding of the first affinity interactor 110 to the second affinity interactor 112 may be substantially irreversible. Once the first and second affinity interactors 110, 112 are bound to each other, the cleavage site 108 enables irreversibly separating the label 114 from the label from the connector 100, or rather from the first affinity reagent 102. The label 114 may be a dye, in particular, one or more fluorophores.

Figure 2:
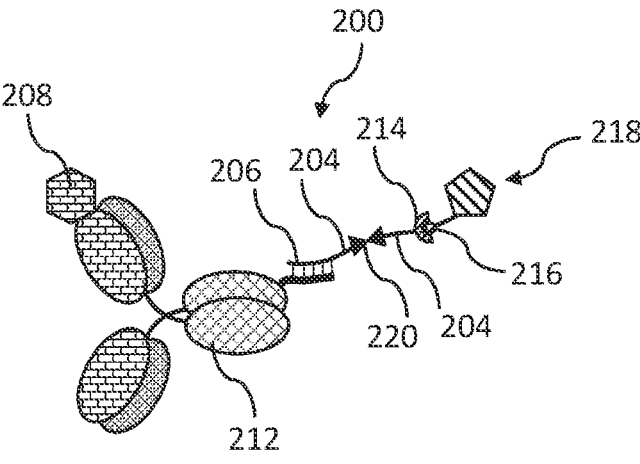
FIG. 2 shows a schematic view of nucleotide-based connectors.
Figure 2:
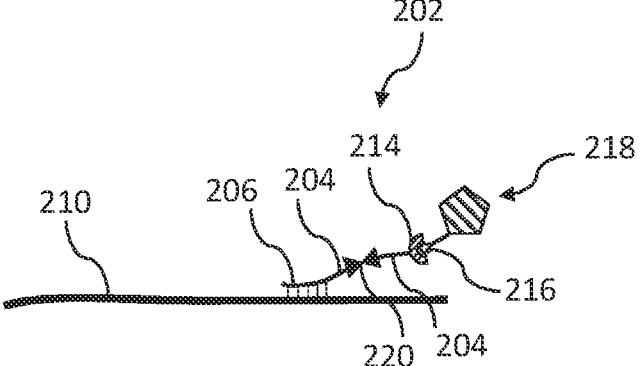
Figure 3:
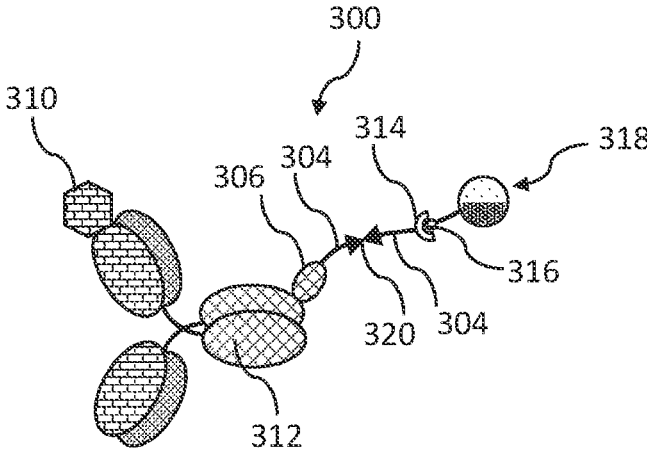
FIG. 3 shows a schematic view of peptide-based connectors.
Figure 3:
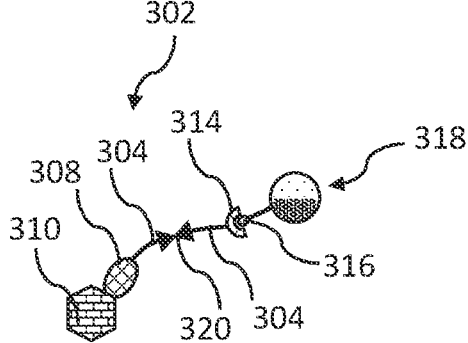

FIGS. 2 and 3 show schematic views of exemplary embodiments of the connector 100.

FIG. 2 shows a schematic view of nucleotide-based connectors 200, 202. The connectors 200, 202 each comprise a backbone 204, which may be an oligonucleotide, in particular a DNA or RNA oligonucleotide, and/or comprise nucleic acid analogues such as PNA, LNA, XNA, and morpholinos. At one end of the backbone 204, the backbone 204 is connected to a first affinity reagent 206, which is oligonucleotide-based, similar to the backbone 204, and which comprise a specific sequence enabling the first affinity reagent 206 to directly or indirectly bind to a target molecule 208, 210.

In case of the connector 200, the first affinity reagent 206 is indirectly bound to the target molecule 208, for example, a protein, via a second affinity reagent 212, such as an antibody. The second affinity reagent 212 comprises, for example, at its fragment crystallisable region (Fc region), an oligonucleotide sequence complementary to the specific sequence of the first affinity reagent 206. The antigen-binding fragment (Fab region) of the second affinity reagent 212 may bind specifically to the target molecule 208. Thus, the connector 200 specifically binds to the target molecule 208 indirectly via the second affinity reagent 212.

Alternatively and in case of the connector 202, the target molecule 210 is an RNA or DNA molecule, for example an mRNA molecule. The first affinity reagent 206 binds to a specific sequence of the target molecule 210 complementary to the sequence of the first affinity reagent 206.

At the other end of the backbone 204, the backbone 204 comprises a first affinity interactor 214 configured to specifically bind to a second affinity interactor 216. The first affinity interactor 214 may, for example, be an oligonucleotide-based aptamer, similar to the backbone 204. The second affinity interactor 216 may be a further aptamer or biotin, for example. The second affinity interactor 216, in turn, is connected to a label 218, such as a dye molecule.

Moreover, the backbone 204 comprises a cleavage site 220. The cleavage site 220 is preferably a restriction site for a restriction enzyme, in particular a rare cutter such as NotI. This enables separating the label 218 from the connector 200, 202.

Since the connector 200, 202, including the first affinity reagent 206, the backbone 204 with the cleavage site 220 and the first affinity interactor 214 are all oligonucleotide-based, the connector 200, 202 may each be synthesised in a single reaction or synthesised in a single piece.

FIG. 3 shows a schematic view of peptide-based connectors 300, 302. The connectors 300, 302 each comprise a backbone 304, which may be a peptide. At one end of the backbone 304, the backbone 304 is connected to a first affinity reagent 306, 308, which are peptide-based, similar to the backbone 304, and which directly or indirectly bind specifically to a target molecule 310.

In case of the connector 300, the first affinity reagent 306 is indirectly bound to the target molecule 310, for example, a protein, via a second affinity reagent 312, such as an antibody. The first affinity reagent 306 is, for example, a nanobody or a single domain antibody, which specifically binds to the second affinity reagent 312, for example, at its fragment crystallisable region (Fc region). The antigen-binding fragment (Fab region) of the second affinity reagent 312 may bind specifically to the target molecule 310. Thus, the connector 300 specifically binds to the target molecule 310 indirectly via the second affinity reagent 312.

Alternatively and in case of the connector 302, the first affinity reagent 308 is, for example, a nanobody or a single domain antibody, which specifically binds directly to the target molecule 310.

At the other end of the backbone 304, the backbone 304 comprises a first affinity interactor 314 configured to specifically bind to a second affinity interactor 316. The first affinity interactor 314 may be peptide-based, similar to the backbone 304, for example, it may be streptavidin. In this case, the second affinity interactor 316 may be biotin, for example. The second affinity interactor 316, in turn, is connected to a label 318, such as a dye molecule. Alternative pairs of first and second affinity interactors 314, 316 that bind specifically to each other may be pairs of peptides that form bioconjugates, such as SpyTag and SpyCatcher, SnoopTag and SnoopCatcher, or DogTag and DogCatcher.

Moreover, the backbone 304 comprises a cleavage site 320. The cleavage site 320 is preferably a specific peptide sequence at which a respective protease, for example, TEV protease from Tobacco etch virus or Factor Xa, or scUlp1 (from *Saccharomyces cerevisiae* with substrate scSUMO), or bdSENP1 (from Brachypodium distachyon with substrate bdSUMO), or bdNEDP1 (from Brachypodium distachyon with substrate bdNEDD8), or sNEDP1 (from Salmo salar with substrate ssNEDD8), or scAtg4 (from *Saccharomyces cerevisiae* with substrate Atg4p), or xlUsp2 (from *Xenopus laevis* with substrate xlUsp2), may cleave the peptide-based backbone 304. This enables separating the label 318 from the connector 300, 302. Full length versions, truncated versions, or fragments of the aforementioned substrates and proteases may be used as cleavage site/protease pair.

In a preferred embodiment of the present invention, bdSENP1 or a bdSENP1 derivative is used to perform cleavage. This provides numerous advantages including very efficient substrate cleavage at concentrations in the nanomolar (nM) regime, i.e. 5 nM at 25° C. or 20-50 nm at 0° for near quantitative cleavage (conditions described in the literature: Steffen Frey, Dirk Gorlich, A new set of highly efficient, tag-cleaving proteases for purifying recombinant proteins, Journal of Chromatography A, Volume 1337, 2014, Pages 95-105), and good activity at temperatures between 0-37° C.

Since the connector 300, 302, including the first affinity reagent 306, the backbone 304 with the cleavage site 320 and the first affinity interactor 314 are all oligonucleotide-based, the connector 300, 302 may each be synthesised by recombinant expression of a single DNA construct and/or synthesised as a continuous single piece.

Alternatively to the first affinity reagents 206,306 discussed in connection with FIGS. 2 and 3, the first affinity reagents 102, 206, 306 may be a multimer of a nanobody or single-domain antibody, a conventional antibody, an aptamer, or a drug, small molecule or toxin.

Alternatively, the cleavage sites 108, 220, 320 may be cleaved by a temperature shift, for example in case the backbone is oligonucleotide-based, in particular a DNA-origami, and the cleavage site is a hybridised part of two oligonucleotide strands, or by activation light, such as UV light, in case the cleavage site is a photocleavable linker.

Figure 4:
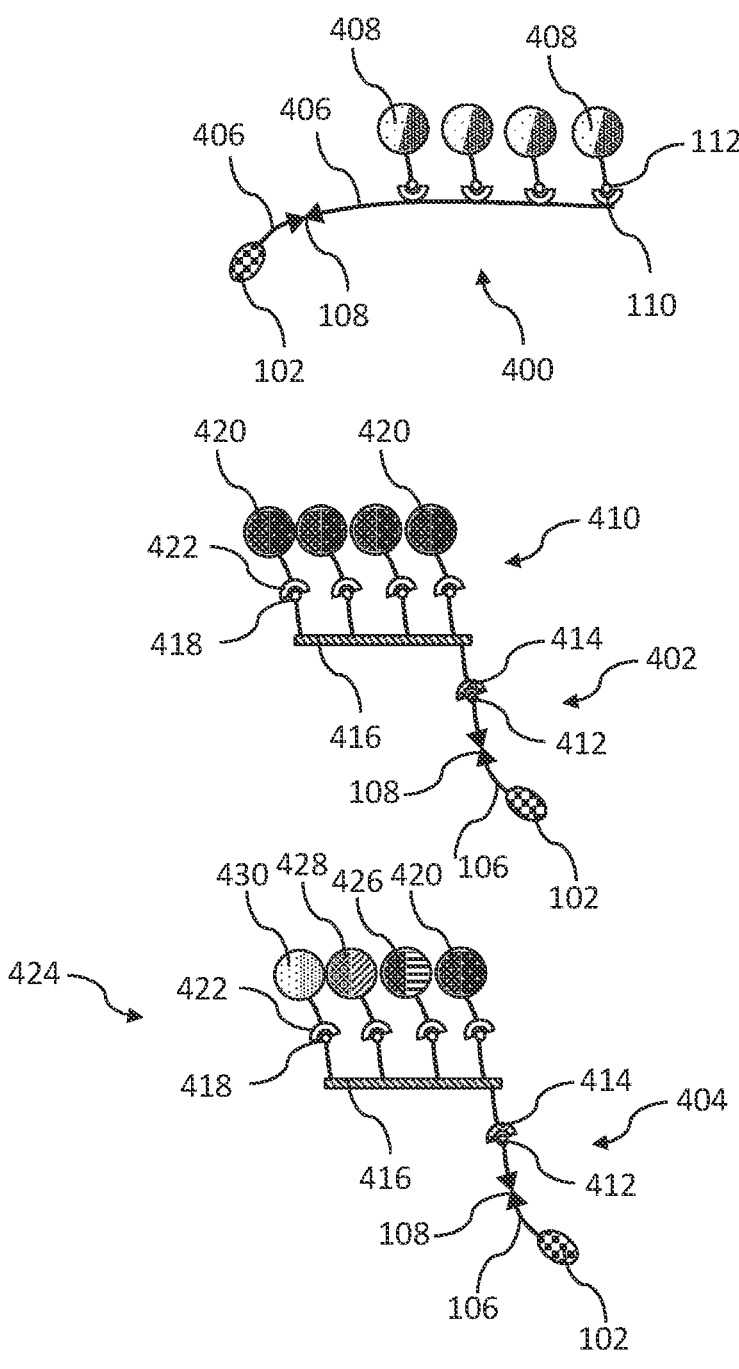
FIG. 4 shows a schematic view of connectors having a label attached.

FIG. 4 shows connector 400, 402, 404 that each have a label attached. Elements with the same structure and the same function have the same reference signs. The connector 400 comprises the first affinity reagent 102, as previously described, the label attached to a backbone 406 of the connector 400 comprises four fluorophores 408. The backbone 406 may, for example, be peptide-based. The backbone 406 comprises four first affinity interactors 110 that are each configured to specifically bind to four second affinity interactors 112 in order to individually attach the fluorophores 408 connected to the second affinity interactors 112. The fluorophores 408 may be attached to the connector 400 by mixing both, the fluorophores 408 with second affinity interactors 112 and the connector 400. As previously described, the first and second affinity interactors 110, 112 may be streptavidin and biotin, respectively, for example.

Connector 402 has a label 410 attached, specifically the label 410 is attached to a first affinity interactor 412 of the connector 402 via a second affinity interactor 414 that specifically binds to the first affinity interactor 412. The label 410 comprises a DNA-origami backbone 416 that is connected to the second affinity interactor 414 and that comprises four first auxiliary affinity interactors 418. The DNA-origami backbone 416 may, for example, be a nanoruler. Four fluorophores 420 are individually attached to backbone 416, by a second auxiliary affinity interactor 422 that specifically binds to the first auxiliary affinity interactor 418 and that is connected to each of the fluorophores 410.

In a preferred embodiment of the present invention, the first and second auxiliary affinity interactor are one of the biotin-streptavidin pair. In this case biotinylated staple strands are allowed to bind to streptavidin-conjugated dyes or fluorophores before the staple strands are allowed to interact with the DNA-origami backbone 416 (preincubation). As the interaction between biotin-streptavidin is practically irreversible this can be leveraged to attach multiple copies of the same dye as in example 402 or multiple dyes (single or multiple copy) as in example 404 to the DNA-origami backbone 416. In this case it may be desirable to use a version of streptavidin with 4, 3, 2 or only one active biotin-binding site.

Connector 404 has a label 424 attached to the first affinity interactor 412 via a second affinity interactor 414, as described for connector 402. Similarly, the label 424 comprises the DNA-origami backbone 416 with four first auxiliary affinity interactors 418. In contrast to the connector 402 with the label 410, the label 424 comprises four fluorophores 420, 426, 428, 430 that each differ in their fluorescent properties. These properties may include excitation wavelength, fluorescent wavelength, and fluorescent duration. Each fluorophore 420, 426, 428, 430 comprises one of the second auxiliary affinity interactors 422 that enable the fluorophores 420, 426, 428, 430 to be attached to one of the first auxiliary affinity interactors 418 of the label 424. By using differing fluorophores 420, 426, 428, 430 in the label 424, connectors with a larger diversity of fluorescent properties may be generated. The diversity of fluorescent properties enables being able to distinguish between a large variety of connectors.

Figure 5:
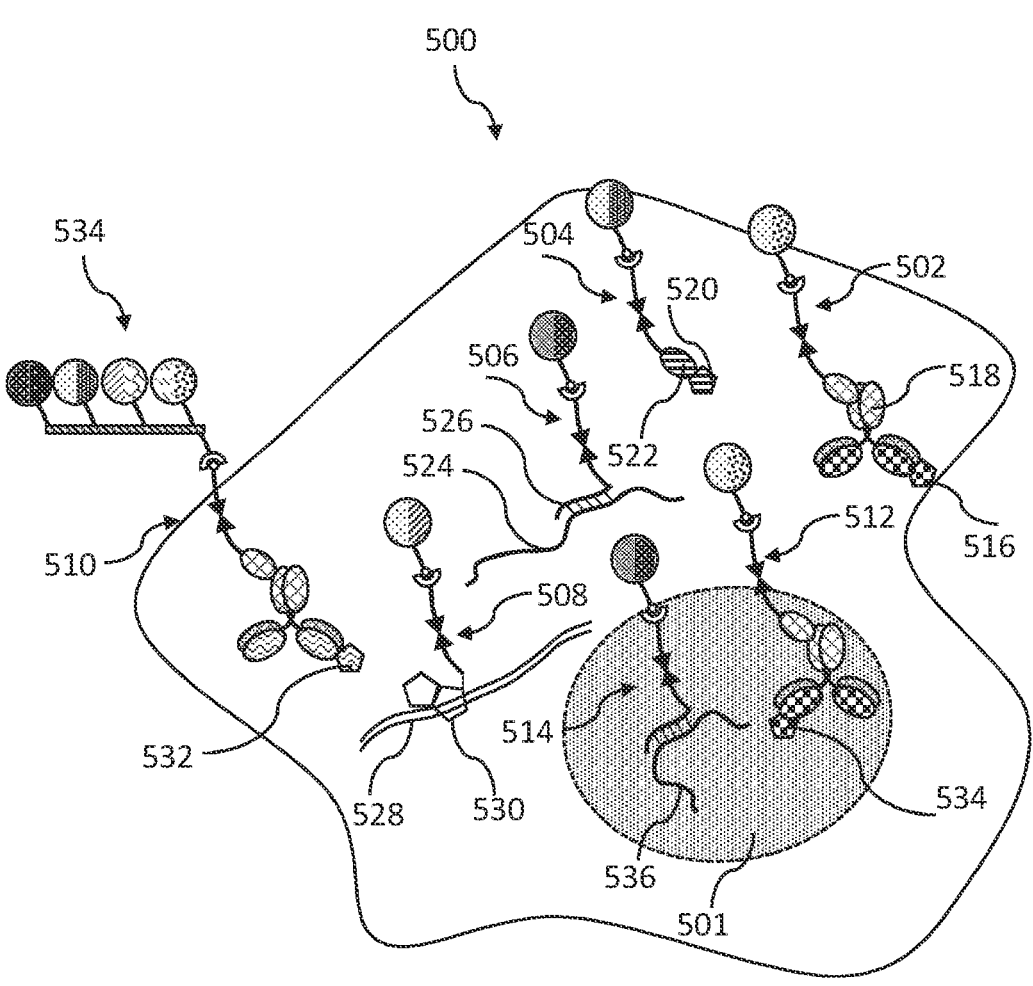
FIG. 5 shows a schematic view of a biological sample with a plurality of connectors.

FIG. 5 shows a schematic view of a biological sample 500 with a plurality of connectors. The biological sample 500 may, for example, be a cell, in particular, a mammalian cell comprising a nucleus 501. Several connectors 502, 504, 506, 508, 510, 512, 514 with labels are used to specifically bind to a particular target molecule in the sample 500, illustrating the use of the labelled connectors. The labels may differ in their fluorescent properties.

For example, connector 502 is indirectly bound to a cytoplasmic protein target molecule 516 via a second affinity reagent 518, here an antibody, and a nanobody first affinity reagent 519. Connector 504 is directly bound to a cytoplasmic protein target molecule 520 via first affinity reagent 522, here a nanobody of the connector 504. Connector 506 is directly bound to a mRNA target molecule 524 via an oligonucleotide-based first affinity reagent 526. The connector 508 is directly bound to a cytoplasmic protein target molecule 528 via a small molecule-based first affinity reagent 530. Similar to connector 502, connector 510 is indirectly bound to a cytoplasmic protein target molecule 532, however, connector 510 is attached to a label 534 comprising a plurality of fluorophores. Similarly to connector 502, connector 512 is indirectly bound to a nuclear protein target molecule 534. Similarly to connector 506, connector 514 is directly bound to a nuclear mRNA target molecule 536.

By means of the connector 502, 504, 506, 508, 510, 512, 514 the individual components 516, 520, 524, 528, 532, 534, 536 of the biological sample 500 may be visualised by fluorescent imaging, for example, of the biological sample 500 with the connector 502, 504, 506, 508, 510, 512, 514 bound to their target molecules. Further, when using distinct labels, with unique fluorescent properties for a particular connector, the components 516, 520, 524, 528, 532, 534, 536 can be localised within the image of the biological sample 500 depending on where a respective fluorescent signal was detected.

As explained above, the combination of one of the connectors with one of the labels specifically bound to the connector via the first and second affinity interactors, may also be termed a marker. This is also the case, when the connector with the label is optionally specifically bound to one of the second affinity reagents. In order to generate the marker, the connector, the label and optionally the second affinity reagents may be mixed together. This allows binding of the label to the connector, more precisely, the binding of the second affinity interactor of the label to the first affinity interactor of the connector and thereby attachment of the label to the connector.

In case the second affinity reagent is to be attached to the connector, the second affinity reagent may be added at the same time, prior or after adding the label. Since the first affinity interactor and the second affinity interactor bind to each other specifically, as do the first and second affinity reagents, the first affinity interactor will only bind to the second affinity interactor, and the first affinity reagent will only bind to the second affinity reagent, even when mixing all components together.

In order to stabilise the binding between the individual parts, the connector and the label and/or the connector and the second affinity reagent may optionally be cross-linked, for example, with glutaraldehyde.

Figure 6:
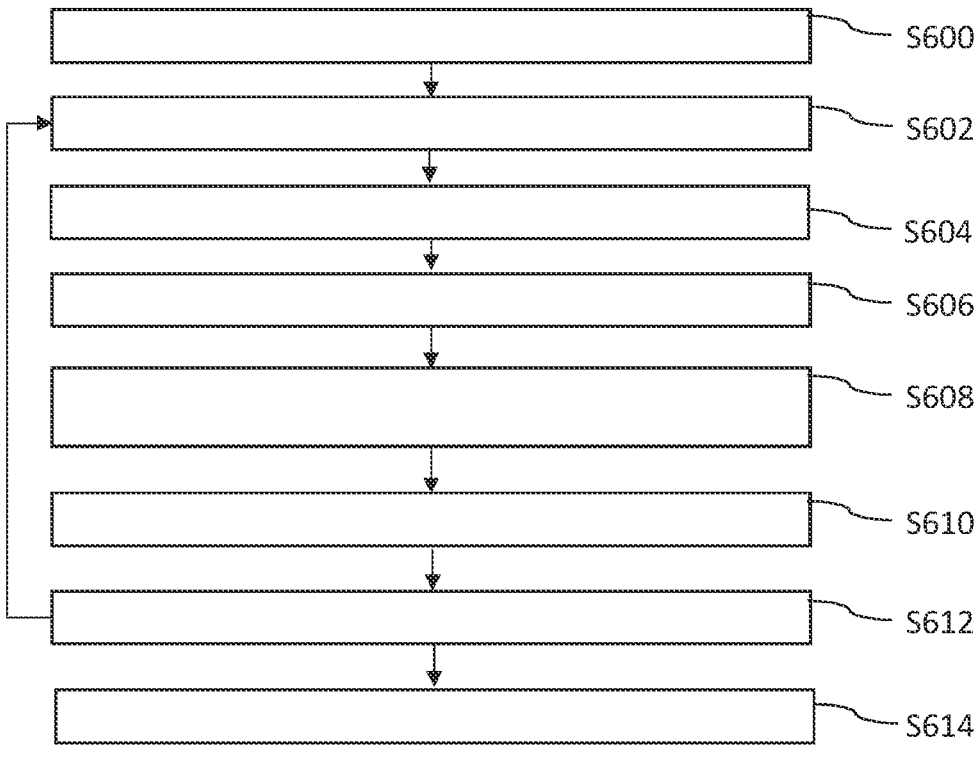
FIG. 6 shows a flowchart for a method for analysing the biological sample.

FIG. 6 shows a flowchart for a method for analysing the biological sample 500, for example, which may be used in the context of multiplex imaging. The process starts in step S600. In step S602 a set of markers is provided. The first set of markers may comprise a first plurality of connectors with a first label and a first affinity reagent configured to specifically bind to a first target molecule. Alternatively, the first plurality of connectors may further comprise a second affinity reagent configured to specifically bind to the first target molecule and the first affinity reagent being configured to bind to the second affinity reagent. Preferably, the first set of markers includes at least a second plurality of connectors with a second label and a first (or second) affinity reagent configured to specifically bind to a second target molecule. The first and second labels have different fluorescent properties such as excitation wavelength, emission wavelength or emission duration.

The step of providing the first set of markers may include generating the markers from the respective connector, the label and optionally the second affinity reagent. This may include mixing the respective connector, the label, and optionally the second affinity reagent, in step S602, as explained above.

In step S604 the sample is stained with the markers. This means that the markers are added to the sample, which causes binding of the affinity reagents to their respective target molecules. Alternatively to mixing the respective connector, the label and optionally the second affinity reagent in step S602, the respective connector, the label and optionally the second affinity reagent may be added individually to the sample in step S604. This is particularly the case, when the marker only comprises a first affinity reagent and not a second affinity reagent. When the connector and the label are introduced into the sample individually, the marker is generated in-situ. The marker then stains the sample by binding to the respective target molecule with the first or second affinity reagent.

In step S606 markers that are not bound to their target molecules are washed out, for example, by washing the sample with a buffer solution. This is to reduce background staining by the label of unbound markers.

In step S608 an image readout is performed, for example, an image of the sample is acquired by illuminating the sample with fluorescent light and capturing the emission light. This may be done by means of a fluorescent microscope. The image reveals locations within the sample of the target molecules, which are stained by a marker with an affinity reagent configured to bind to the particular target molecule.

In step S610 the label is separated from the connector by cleaving of the cleavage site of the connector. This removes the fluorescent signal from the target molecule that the marker is bound to. This may also be called blanking.

In step S612 the cleaved off label is washed out of the sample, for example, by washing the sample with the buffer solution. The method ends in step S614.

Alternatively to ending the method in step S614, the method may proceed by repeating steps S602 to S612 with a different set of markers. This enables using a new set of connectors with affinities to further target molecules whilst at least partially using labels with the same fluorescent properties as the first set of markers. By iterating through steps S602 to S612 repeatedly, a number of target molecules larger than the number of markers with unique fluorescent properties may be stained, imaged and localised.

The connector, or the markers as described herein, may further be used in conjunction with methods and workflows for analysing biological samples disclosed in applications PCT/EP2021/066645 and PCT/EP2021/073819, the contents of which are incorporated herein in their entireties.

Figure 7:
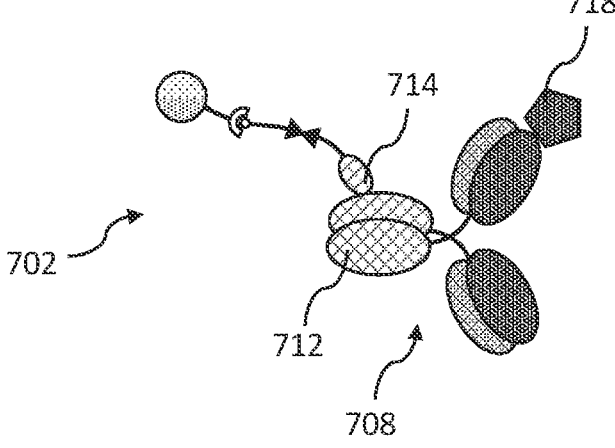
FIG. 7 shows a schematic view of markers with antibodies of the same isotype.
Figure 7:
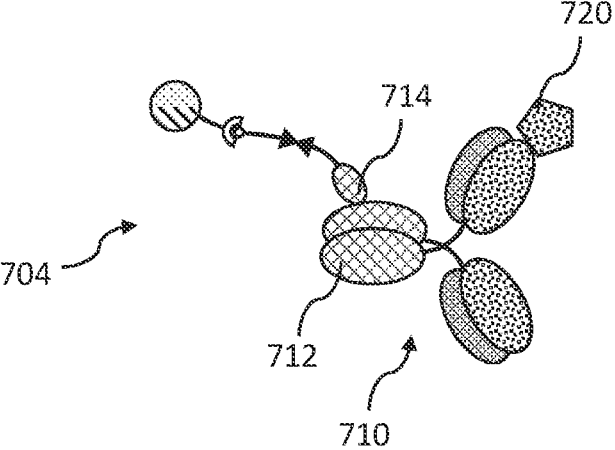

FIG. 7 shows a schematic view of several markers 700, 702, 704. The markers 700, 702, 704, comprise antibodies 706, 708, 710 of the same isotype as second affinity reagents. This means, their Fc region 712 is the same. The first affinity reagents 714 bind to the Fc region 712 of the antibodies 706, 708, 710. This means that based on one type of connector comprising only the same first affinity reagent 714, markers may be generated that nevertheless bind specifically to different target molecules 716, 718, 720. Further, this allows using antibodies of the same isotype in a single set of markers. The markers 700, 702, 704 have to be prepared separately to avoid mixing the different antibodies 706, 708, 710 and labels.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

100, 200, 202, 300,
302, 400, 402, 404,
502, 504, 506, 508,
510, 512, 514 Connector
102, 206, 306, 308,
522, 526, 530, 714 First affinity reagent
104, 208, 210, 310,
516, 520, 524, 528,
532, 534, 536, 716,
718, 720 Target molecule
106, 204, 304, 406 Backbone
108, 220, 320 Cleavage site
109 Enzyme
110, 214, 314, 412 First affinity interactor
112, 216, 316, 414 Second affinity interactor
114, 218, 318, 410,
424, 534 Label
212, 312, 518 Second affinity reagent
408, 420, 426, 428,
430 Fluorophore
416 DNA-origami backbone
418 First auxiliary affinity interactor
422 Second auxiliary affinity interactor
500 Biological sample
501 Nucleus
700, 702, 704 Marker
706, 708, 710 Antibody
712 Fc region of antibody

The invention claimed is:

1. A set of markers for analysing biological samples, each marker comprising a connector and a label with a second affinity interactor, the connector comprising:
   at least one first affinity reagent configured to bind indirectly to a target molecule,
   a second affinity reagent bound to the first affinity reagent, wherein the second affinity reagent is configured to bind to the target molecule, wherein the second affinity reagent is an antibody, and the first affinity reagent is configured to bind to a fragment crystallisable (Fc) region of the antibody, and
   a backbone connected to the first affinity reagent and comprising at least one first affinity interactor,
   wherein the first affinity interactor is configured to specifically bind to a second affinity interactor comprising the label in order to bind the label to the backbone,
   wherein the backbone comprises a cleavage site for irreversibly separating the first affinity reagent and the first affinity interactor, and
   wherein antibodies of the markers of the set of markers are of a same isotype having the same Fc region that binds to the first affinity reagent, and wherein the antibodies are specific to different target molecules.

2. The set of markers according to claim 1, wherein the first affinity reagent is a nanobody, or an aptamer.

3. The set of markers according to claim 1, wherein the backbone comprises an oligonucleotide or a peptide.

4. The set of markers according to claim 1, wherein the cleavage site is a photocleavable cleavage site.

5. The set of markers according to claim 1, wherein the backbone is cleavable specifically at the cleavage site by an enzyme, cleavage light, or by a temperature change.

6. The set of markers according to claim 1, wherein the first affinity interactor and the second affinity interactor are configured to form a bioconjugate.

7. The set of markers according to claim 1, wherein the first affinity interactor is one of biotin or streptavidin, and the second affinity interactor is the other one of biotin or streptavidin.

8. The set of markers according to claim 1, wherein the connector comprises a plurality of first affinity interactors for binding a plurality of second affinity interactors.

9. The set of markers according to claim 1, wherein the label comprises at least a first fluorophore.

10. A method for analysing a biological sample comprising the following steps:
   a) providing at least a first set of markers, including the set of markers according to claim 1, wherein the first set of markers comprises at least a first plurality of connectors configured to bind directly or indirectly to a first target molecule, and each first connector comprising a first label,
   b) introducing at least the first set of markers into the sample in order for the markers to bind to their respective target molecule in the sample,
   c) directing excitation light onto the biological sample, the excitation light being configured to visualise at least the first label, and
   d) generating at least one optical readout from light emitted by at least the first label.

11. The method according to claim 10, wherein the first set of markers further comprises at least a second plurality of connectors configured to bind directly or indirectly to a second target molecule, and each second connector comprising a second label.

12. The method according to claim 11, wherein the first label and the second label have different fluorescent properties.

13. The method according to claim 10, wherein in a step e) cleavage site of the connectors of at least the first set of markers is cleaved.

14. The method according to claim 13, wherein in a step f) cleaved off second affinity interactor is removed.

15. The method according to claim 13, wherein the steps a) to d) are repeated with a second set of markers, wherein the second set of markers comprises at least a third plurality of connectors configured to bind directly or indirectly to a third target molecule, and each connector comprising a third label.

* * * * *